United States Patent
Al-Jarba

(10) Patent No.: US 11,071,815 B1
(45) Date of Patent: Jul. 27, 2021

(54) DISPOSABLE STERILE COVER FOR EAR WASHING MACHINES

(71) Applicant: Meshil A. M. O. H. Al-Jarba, Safat (KW)

(72) Inventor: Meshil A. M. O. H. Al-Jarba, Safat (KW)

( * ) Notice: Subject to any disclaimer, the term of this patent is extended or adjusted under 35 U.S.C. 154(b) by 0 days.

(21) Appl. No.: 17/087,589

(22) Filed: Nov. 2, 2020

(51) Int. Cl.
*A61M 3/02* (2006.01)

(52) U.S. Cl.
CPC ... *A61M 3/0279* (2013.01); *A61M 2205/0205* (2013.01); *A61M 2205/11* (2013.01); *A61M 2209/00* (2013.01); *A61M 2210/0662* (2013.01)

(58) Field of Classification Search
CPC .............. A61M 3/0279; A61M 3/0233; A61M 2205/0205; A61M 2205/11; A61M 2209/00; A61M 2210/0662; A61F 6/04; A61F 13/105; G01K 1/083; A61J 11/008
See application file for complete search history.

(56) References Cited

U.S. PATENT DOCUMENTS

| | | | | |
|---|---|---|---|---|
| 2,789,560 | A * | 4/1957 | Weimer | A61F 5/453 604/349 |
| 4,738,673 | A * | 4/1988 | Shepard | A61F 6/04 604/327 |
| 5,579,784 | A * | 12/1996 | Harari | A61F 6/00 128/844 |
| 5,662,605 | A | 9/1997 | Hurwitz | |
| 5,685,851 | A * | 11/1997 | Murphy | A61M 3/022 604/150 |
| 5,833,675 | A | 11/1998 | Garcia | |
| 5,944,711 | A | 8/1999 | Pender | |
| 6,485,451 | B1 | 11/2002 | Roberts et al. | |
| 8,187,236 | B1 | 5/2012 | French | |
| 2006/0253087 | A1 | 11/2006 | Vlodaver et al. | |

FOREIGN PATENT DOCUMENTS

CN  207996259 U  10/2018

OTHER PUBLICATIONS

"Welch Allyn 29360-1 Disposable Eartips for the Ear Wash System—Box of 25," © Copyright 2010-2020 Tiger Medical, Inc.: https://www.tigermedical.com/Products/Disposable-Eartips-for-the-Ear-Wash-System--Box-of-25_WEL29360-1.aspx?invsrc=adwords_tm&gclid=EAlalQobChMI6PHzvteg5AlVtl1bCh1ctgn_EAQYAyABEgL7mfD_BwE.

"1 144-Piece Size M, 4-¼" Long, Medical Use Finger Cot," © 2000-2020 MSC Industrial Direct Co., Inc.: https://www.mscdirect.com/browse/tnpla/97834816?cid=ppc-google-New+-+Safety+-+PLA_sv35fxxs9__164110844835_c_S&mkwid=sv35fxxs9|dc&pcrid=164110844835&rd=k&product_id=97834816&gclid=EAlalQobChMlkbHxu_el5AlVClzlCh1F4wWdEAQYAyABEgKJkfD_BwE.

* cited by examiner

*Primary Examiner* — Nathan R Price
*Assistant Examiner* — Justin L Zamory
(74) *Attorney, Agent, or Firm* — Nath, Goldberg & Meyer; Richard C. Litman

(57) ABSTRACT

The disposable protective cover for ear washing machines is designed to protect a patient's ear from bacteria or infection during use of the machine. The cover is a flexible, resilient tube having an open end and a reinforced ring about the open end. The opposite end of the tube is hemispherical and closed, but having a central, circular opening for ear washing solution from the ear washing machine to exit the cover and enter the ear. To place the cover on the ear washing machine's nozzle, the cover is first rolled up to form a disc and the protective cover is placed against the nozzle with the central opening aligned with the nozzle's circular outlet port. It is then unrolled as much as possible over the outer (Continued)

surface of the nozzle. The protective cover is disposed of after each use to prevent the spread of bacteria or infection between patients.

2 Claims, 5 Drawing Sheets

DISPOSABLE STERILE COVER FOR EAR WASHING MACHINES

BACKGROUND

1. Field

The disclosure of the present patent application relates to external ear care, and particularly to a disposable sterile cover for ear washing machines.

2. Description of the Related Art

Washing ears is an important part of personal hygiene. In addition, for patients with ear infections and other maladies of the ear, daily ear washing may be necessary. In a clinical setting, the ear washing is often performed using an ear washing machine. The ear washing machine includes a nozzle that is in the form of a metallic, cylindrical tube with a hemispherically shaped distal end. An ear washing solution is sprayed from a central circular port on the distal end of the nozzle. The nozzle often contacts the patient's ear canal, and is also contacted by back spray of the solution as it is reflected by the ear. If the nozzle is not properly sterilized, bacteria and infection can be transferred between patients.

Thus, a disposable sterile cover for ear washing machines solving the aforementioned problems is desired.

SUMMARY

The disposable sterile cover for ear washing machines is designed to protect a patient's ear from bacteria or infection during use of the machine. The cover is a flexible rubber tube having an open end and a reinforced ring about the open end. The distal end of the tube is semi-spherical and has a central circular opening permitting ear washing solution from the ear washing machine to exit the cover and enter the patient's ear. To place the cover on the ear washing machine's spray nozzle, the cover is first rolled up to form a disc (alternatively, the cover may be supplied rolled up, to avoid the need for this initial step in the doctor's office). The protective cover is then placed against the nozzle with the central opening aligned with the nozzle's circular outlet port. It is then unrolled over the outer surface of the nozzle, until it is unrolled as much as possible. The protective cover is disposed of after a single use to prevent the spread of bacteria or infection between patients.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
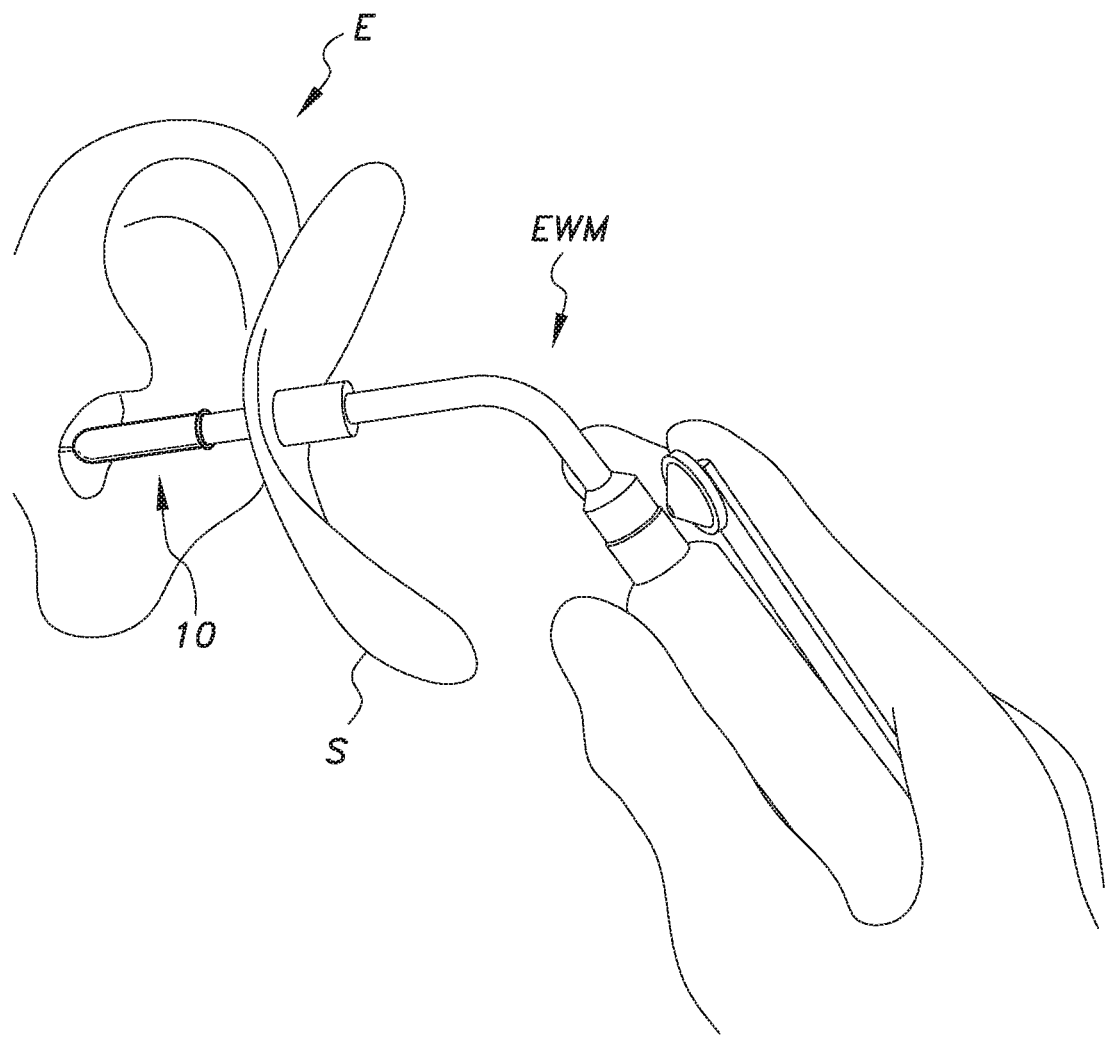
FIG. 1 is an environmental perspective view of a disposable sterile cover for ear washing machines, shown mounted on the nozzle of an irrigation tube of an ear washing machine used to wash a patient's ear.
Figure 2:
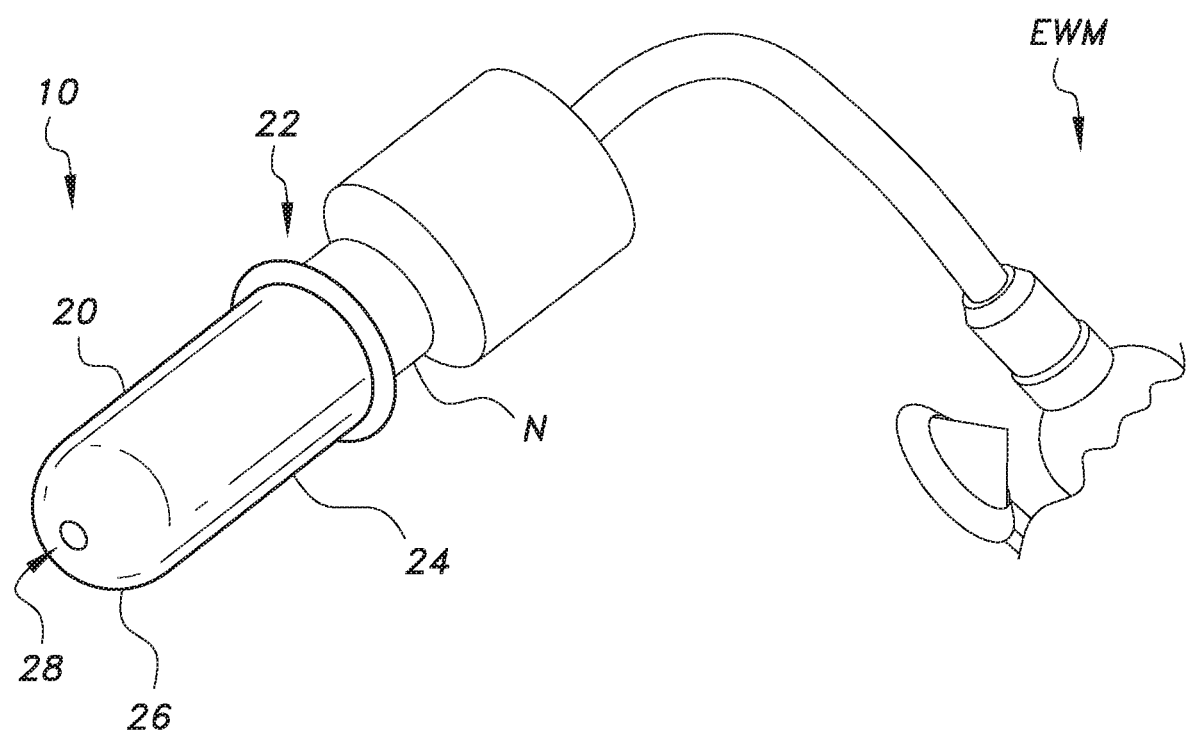
FIG. 2 is a partial environmental perspective view of the irrigation tube of an ear washing machine having the disposable sterile cover of FIG. 1 mounted on the nozzle of the irrigation tube.
Figure 3:
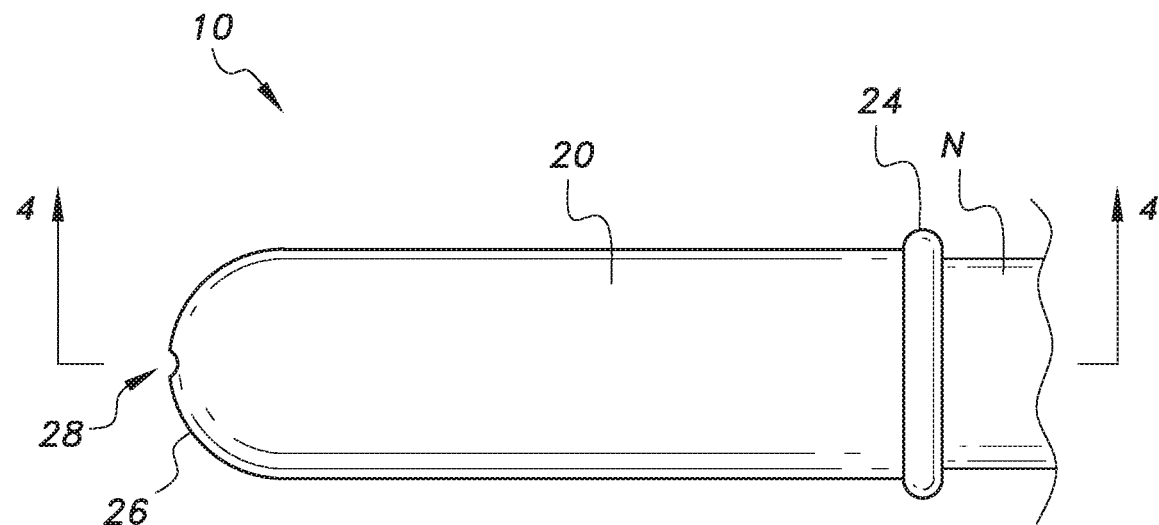
FIG. 3 is an environmental side view of the irrigation tube of FIG. 1, showing the disposable sterile cover mounted on the nozzle of the tube.
Figure 4:
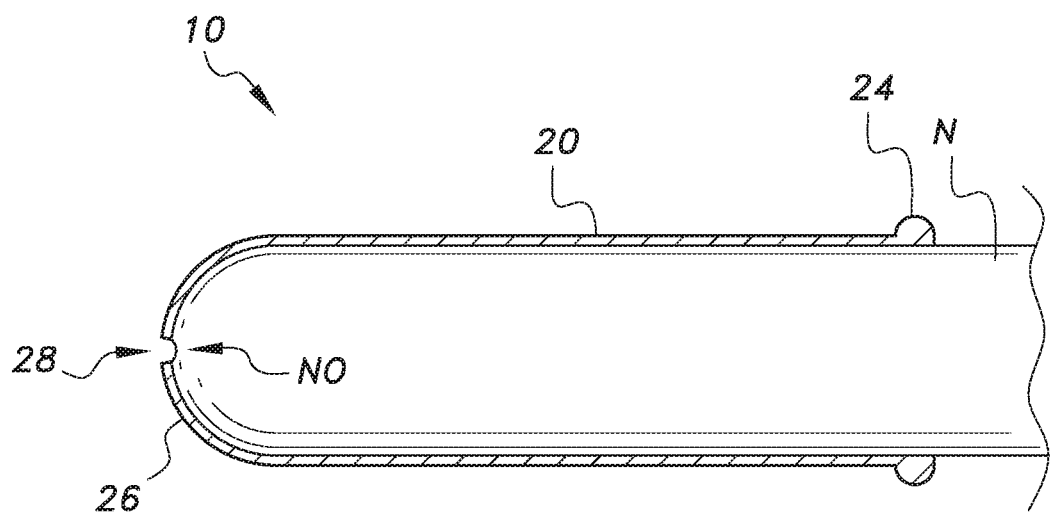
FIG. 4 is a section view along lines 4-4 of FIG. 3.

The disposable protective cover for ear washing machines 10 is shown in FIGS. 1-4 mounted on the nozzle N of the irrigation tube of an ear washing machine EWM that is being used to wash an ear E of a patient. The cover 10 has a flexible, resilient, cylindrical tube main portion 20 having an open end and an integral reinforced ring 24 about the open end. The opposite end 26 of the tube 20 is closed and hemispherical to conform to the nozzle N of the irrigation tube or fluid delivery tube of the ear washing machine EWM. A central, circular opening 28 at the closed end 26 of the tube 20 aligns with a nozzle opening NO at the end of the nozzle N (see FIG. 4) to allow ear washing solution from the ear washing machine to exit the cover 10 and enter the patient's ear E. The cover 10 is a one-piece device that can be made of rubber, latex, or other polymeric material.

Figure 5:
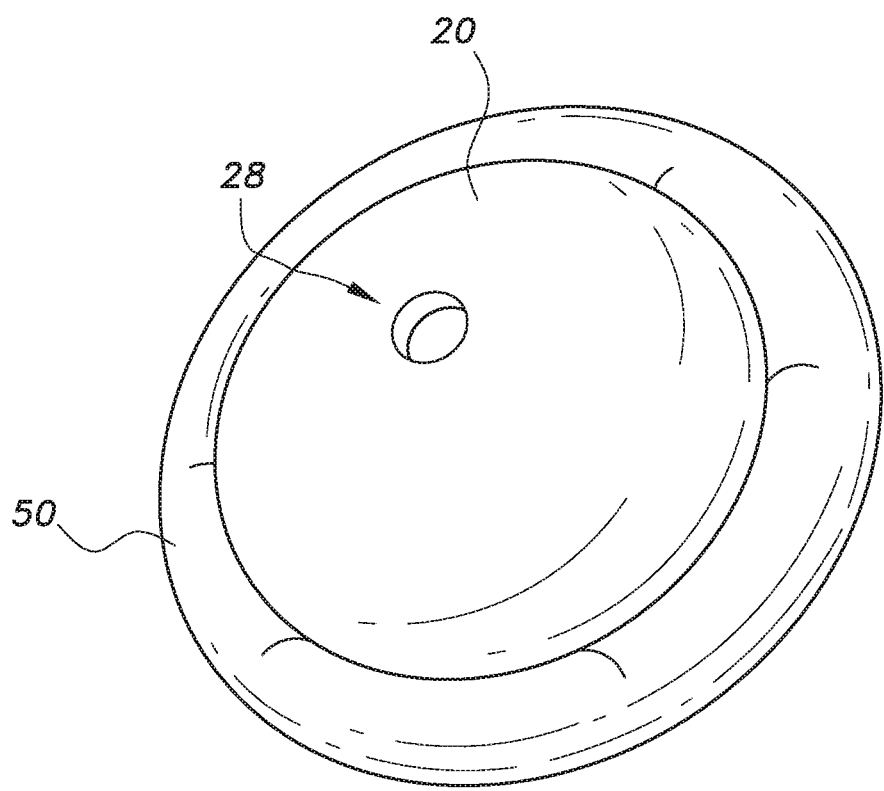
FIG. 5 is a perspective, view of the disposable sterile cover for ear washing machines of FIG. 1, shown in a rolled-up, disc-shaped configuration.
Figure 6:
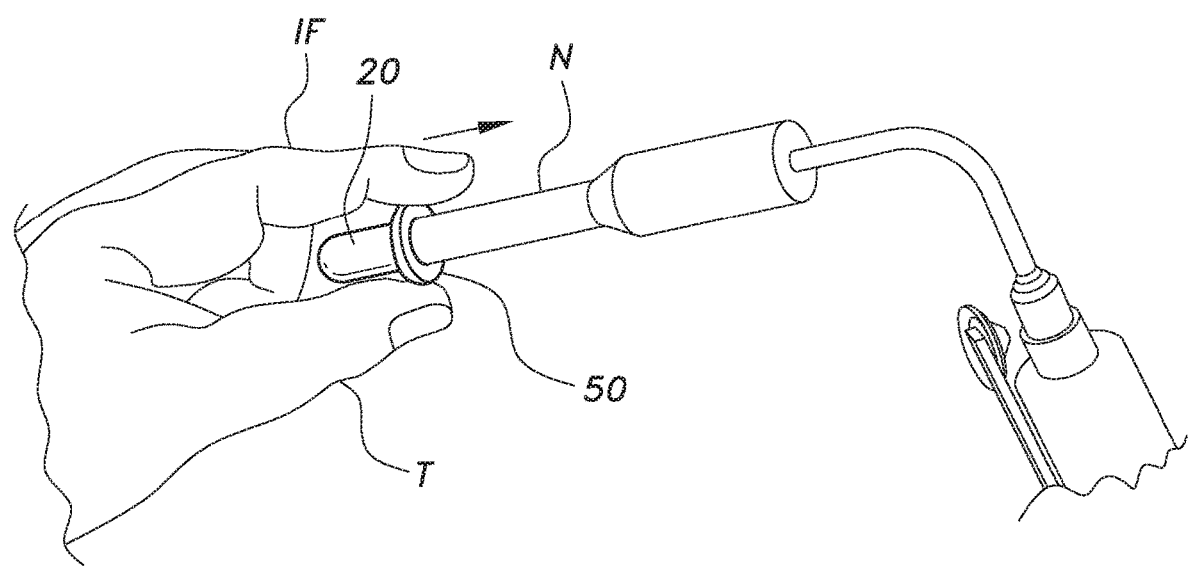
FIG. 6 is an environmental perspective view showing the disposable sterile cover of FIG. 1 being installed on the nozzle of the irrigation tube of an ear washing machine.

FIG. 5 shows the disposable sterile cover 10 in a rolled-up, flat, disc-shaped configuration, wherein a portion 50 of the cylindrical tube main portion 20 is wrapped around the reinforced ring 24. The cover 10 can be packaged in this configuration with several covers 10 in a single package. FIG. 6 shows a method of installing the disposable sterile cover 10 on the nozzle N of the irrigation tube of an ear washing machine EWM to protect a patient from bacteria or infection from the ear washing machine EWM. To place the cover 10 on the ear washing machine's spray nozzle N, the cover 10 is first rolled up to form the rolled-up, flat, disc-shaped configuration of FIG. 5. Alternatively, as described above, the cover 10 may be supplied in its rolled-up, flat, disc-shaped configuration to avoid the need for this initial step in the doctor's office. The protective cover 10 is then placed against the end of the nozzle N with the central opening 28 aligned with the nozzle's circular outlet port NO. It is then unrolled over the outer surface of the nozzle N using the thumb T and index finger IF of a single hand. The cover 10 is unrolled completely until the reinforced ring 24 is visible, or as much as possible should the particular nozzle N have an obstruction thereon. After use, the protective cover 10 can be removed by simply pulling it of the nozzle N in a reverse motion using the thumb T and index finger IF. The covers 10 are disposed of after each use of the ear washing machine EWM to prevent the spread of bacteria or infection between patients.

It is to be understood that the disposable sterile cover for ear washing machines is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for protecting a patient from bacteria and infections from contact with an ear washing machine irrigation tube having a nozzle for dispensing an ear washing fluid, the method comprising the steps of:

providing a one-piece, disposable sterile cover having a flexible, resilient, cylindrical tube main body portion having an open end and an integral reinforced ring about the open end, and an opposite closed end having a central, circular opening defined therein;

rolling up the cover to form a rolled-up, flat, disc-shaped configuration;

placing the protective cover against the nozzle end of the irrigation tube;

aligning the central opening of the cover with the nozzle's outlet port; and unrolling the cover over the nozzle end of the irrigation tube.

2. The method for protecting a patient according to claim 1, further comprising the step of disposing of the cover after a single use.

* * * * *